United States Patent [19]

Brossi et al.

[11] 4,390,699
[45] Jun. 28, 1983

[54] 6-KETO-MORPHINANS BELONGING TO THE 14-HYDROXY-SERIES

[75] Inventors: Arnold Brossi; Helmut Schmidhammer, both of Bethesda; Arthur E. Jacobson, Potomac, all of Md.

[73] Assignee: The United States of America as represented by the Secretary of the Department of Health and Human Services, Washington, D.C.

[21] Appl. No.: 284,089

[22] Filed: Jul. 16, 1981

[51] Int. Cl.$^3$ .................. C07D 221/28; A61K 31/485
[52] U.S. Cl. ..................... 546/74; 424/260; 546/45
[58] Field of Search ........................... 546/74; 424/260

[56] References Cited

U.S. PATENT DOCUMENTS 3,914,233  10/1975  Mohacsi et al. ..................... 546/74

FOREIGN PATENT DOCUMENTS 40-20863  9/1965  Japan ..................... 546/74
41-6905   4/1966  Japan ..................... 546/74

OTHER PUBLICATIONS

Hsu et al., Heterocycles, 1979, 13 (Spec. Issue), 259-61.
Hsu et al., Helv. Chim. Acta, 1980, 63 (7), 2042-5.
Rozwadowska et al., Can. J. Chem., 1980, 58 (17), 1855-9.
Zakrzewski, Chemical Abstracts, vol. 76, 50006w, (1972).
Schmidhammer et al., Helvetica Chimica Acta, vol. 64, No. 8, pp. 2540-2543, (1981).
Zakrzewski (I), Farmacja Polska, vol. 27, No. 9, pp. 695-698, (1971).
Brossi et al., Chemical Abstracts, vol. 95, 187481j, (1981).
Reden et al., J. Med. Chem., vol. 22, No. 3, pp. 256-259, (1979).
Chemical Abstracts, vol. 76, Chemical Subject Index (E-O), Jun. 30, 1972, morphinan, morphinan-6-one.

*Primary Examiner*—Nicholas S. Rizzo
*Assistant Examiner*—Diana G. Rivers
*Attorney, Agent, or Firm*—John S. Roberts, Jr.

[57] ABSTRACT

6-Keto-hydroxymorphinans having at the 4 position a substituent which is $R_1 = H$, O lower alkyl, or O lower acyl, and N may be substituted by $R_2$, which for agonist properties may be lower alkyl, lower alkenyl, cyclopropylmethyl, or phenyl lower alkyl, etc. Additionally, the nitrogen may be substituted by $R_2$, which is allyl, cyclopropylmethyl, cyclobutylmethyl, dimethylallyl, etc., which function as antagonists to the morphine-like activity of the compound. Such activity is known as antinociceptive.

8 Claims, No Drawings

6-KETO-MORPHINANS BELONGING TO THE 14-HYDROXY-SERIES

The present invention describes the products and preparation of novel 4-methoxy-14-hydroxy-6-ketomorphinans which are substituted on the nitrogen with groups favoring narcotic agonist properties and with groups favoring narcotic antagonist properties. Additional substitutions at the 4 position and at the nitrogen are shown in the formula below and pharmaceutically acceptable acid addition salts thereof

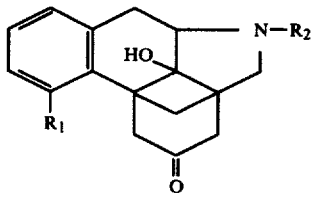

I $R_1$ = H, O lower alkyl, O lower acyl
$R_2$ = Lower alkyl, lower alkenyl, cyclopropylmethyl, Ph lower alkyl The particular ketomorphinan structures above have morphine analgesic properties and by substitution on the nitrogen with alkyl groups, such as methyl, or aralkyl, such as phenethyl, give narcotic agonist properties. It is further noted that in the preparation and in the properties of the compounds of these 4-methoxy-14-hydroxy-6-ketomorphinans, substitution on the nitrogen with proper groups produces narcotic antagonist activities, such as allyl, cyclopropylmethyl, cyclobutylmethyl, dimethylallyl, etc.

The relationship of these morphinan compounds to morphine is shown by the formula below:

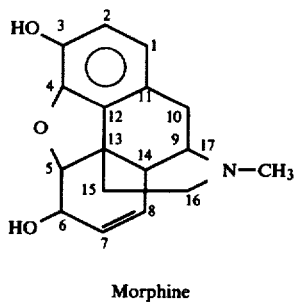

Morphine

TABLE

Structures of Opioids and Opioid Antagonists Chemically Related to Morphine

| Non-proprietary Name | Chemical Radicals and Positions | | | Other Changes# |
|---|---|---|---|---|
| | 3* | 6* | 17* | |
| Morphine | —OH | —OH | —CH₃ | — |
| Heroin | —OCOCH₃ | —OCOCH₃ | —CH₃ | — |
| Hydromorphone | —OH | =O | —CH₃ | (1) |
| Oxymorphone | —OH | =O | —CH₃ | (1),(2) |
| Levorphanol | —OH | —H | —CH₃ | (1),(3) |

*The numbers 3, 6, and 17 refer to positions in the morphine molecule, as shown above.
Other changes in the morphine molecule are:
(1) Single instead of double bond between C7 and C8
(2) OH added to C14
(3) No oxygen between C4 and C5

The subject material are crystalline bases which can be converted into water-soluble acid addition salts, such as hydrochlorides, hydrobromides, phosphates, sulfates, tartrates, succinates, etc. The compounds as produced are orally useful but in the form of their water-soluble acid addition salts can also be used as injectables. Of first importance of the present series of compounds are those in which the antagonist side chain is allyl, cyclopropylmethyl, dimethylallyl or cyclobutylmethyl.

This series of compounds originated from oxymorphone (3,14-dihydroxy-6-ketodihydromorphine) and therefore the stereochemistry belongs to the natural series:

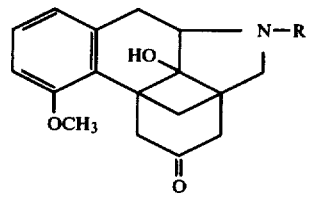

II

R = methyl, phenethyl, allyl, cycloalkylmethyl, dimethylallyl, alkynyl, H.

The 6-ketomorphinans covered in this application can either be made from natural opioids, such as morphine or thebaine, or by total synthesis. In the preparation from natural opioids the 6-ketomorphinans obtained contain the stereochemistry required for the binding to the opiate receptor and thus for the noted antinociception. This stereochemistry is shown in Formula II above.

If the compounds are being prepared by total synthesis racemic mixtures are being obtained which have to be resolved. A preferred way of making optically active ketomorphinans of the required stereochemistry from racemic mixtures lies in the chemical resolution of appropriately substituted tetrahydroisoquinolines. These intermediates contain 1 asymmetric carbon atom only and, by treating the free base with an optically active resolving agents such as tartaric acids, tartranilic acids, substituted tartaric acids, mandelic acids, etc., afford salts of the wanted optical isomer which can be isolated. Either one of the two optically active tetrahydroisoquinolines, belonging either to the (+)- or (−)-series, can be processed, but it is only one which will give the required ketomorphinan belonging to the (−)-series of opioids. The other optical isomer will give a compound belonging to the unnatural (+)-series of ketomorphinans which has no antinociceptive properties but may have other valuable biological qualities. The total synthesis covers by itself the preparation of ketomorphinans belonging to the (−)- and (+)-series.

Chemical resolution can also be carried out at the stage of the 6-ketomorphinans affording (−)- and (+)-enantiomers.

Of course, where oxymorphone is a synthetic starting point, then the compounds produced will be initially inactive as racemates which can then be broken up into the natural and unnatural isomers which can be separated.

The compounds of this series have been shown to have high antinociceptive potency as analgesics. For example, this compound (4-methoxy-14-hydroxy-6-ketomorphinan) is about seven times more active in the hot plate assay in mice than morphine after subcutaneous appliation and the following compounds are illustrative of the present invention:

(−)-4-methoxy-14-hydroxy-6-keto-N-methylmorphinan
(−)-4-methoxy-14-hydroxy-6-keto-N-allylmorphinan
(−)-4-methoxy-14-hydroxy-6-keto-N-cyclopropylmethylmorphinan
(−)-4-methoxy-14-hydroxy-6-keto-N-cyclobutylmethylmorphinan
(−)-4-methoxy-14-hydroxy-6-keto-N-morphinan
(−)-4-methoxy-14-hydroxy-6-keto-N-cyclopropylcarbonylmorphinan
(−)-14-hydroxy-6-keto-N-methylmorphinan
(−)-14-hydroxy-6-keto-N-allylmorphinan
(−)-14-hydroxy-6-keto-N-cyclopropylmethylmorphinan

PRIOR ART STATEMENT

Jacobson et al., *Helvetica Chimica Acta*, July, 1981.

U.S. Pat. No. 3,166,559 Sawa et al.—shows 14-hydroxy-N-methylmorphinans.

U.S. Pat. No. 4,161,597 Olofson et al.—shows 14 hydroxy compounds.

U.S. Pat. No. 4,260,617 Razdan et al.—shows 14 hydroxy-3-methoxymorphinan-6-one.

For purposes of this application and claims, as noted in Formula II, substitution on the nitrogen with antagonist groups, such as allyl, cyclopropylmethyl, cyclobutylmethyl, and dimethylallyl, is intended to embrace $C_1$–$C_6$ type compounds where pertinent. Likewise, where the nitrogen is substituted with methyl, ethyl, propyl, phenethyl to produce narcotic agonists, then this specification and claims embrace $C_1$–$C_6$ compounds. Furthermore, pharmaceutically acceptable acid addition salts such as hydrochlorides, hydrobromides, phosphates, sulfates, tartrates, succinates are included with the free base.

EXAMPLE 1

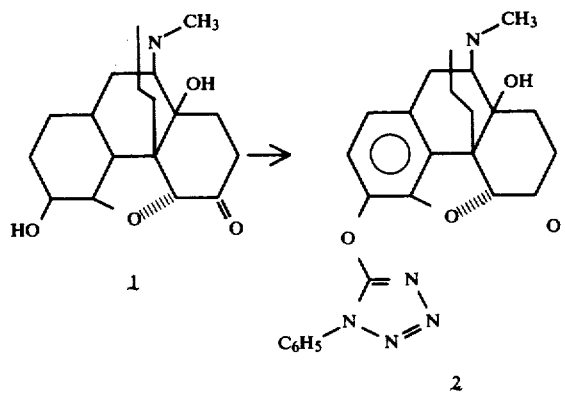

4,5-Epoxy-14-hydroxy-N-methyl-3-(1-phenyl-1H-5-tetrazolyloxy)morphinan-6-one

A mixture of 2.4 g (79.6 mmol) oxymorphone, 24 g (173.6 mmol) anhydrous $K_2CO_3$ and 14.55 g (80.1 mmol) 5-chloro-1-phenyl-1H-tetrazole in 300 ml dry DMF was stirred at room temperature under argon for 20 hours. Then the reaction mixture was filtered, washed with $CHCl_3$ and the filtrate was evaporated in vacuo. The oily residue was dissolved in 200 ml $CHCl_3$, extracted with 1 N NaOH, water and brine. The organic layer was dried and evaporated to give 47.5 g of an oil, which was converted to the oxalate salt to yield 41.5 g (91%) of 4,5-epoxy-14-hydroxy-N-methyl (-3-(1-phenyl-1H-5-tetrazolyloxy) morphinan-6-one.(-$CO_2H)_2$.$2H_2O$, m.p. 143°–148°. The base was crystallized with ethyl acetate, m.p. 99°–102°, $[\alpha]_D$—179.0° (C 0.83, $CHCl_3$).

EXAMPLE 2

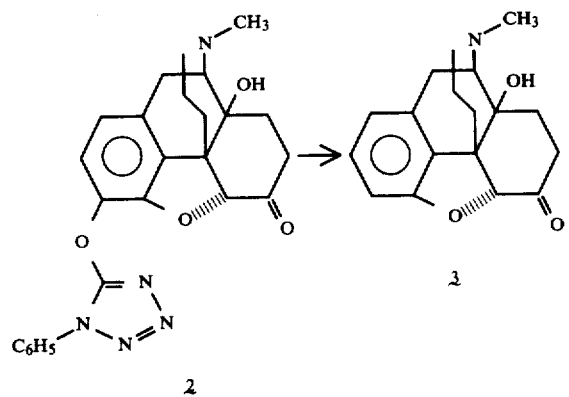

4,5-Epoxy-14-hydroxy-N-methylmorphinan-6-one

To a solution of 9.5 g (16.6 mmol) 4,5-epoxy-14-hydroxy-N-methyl-3-(1-phenyl-1H-5-tetrazolyloxy)-morphinan-6-one.($CO_2H)_2$.$2H_2O$ in 110 ml glacial acetic acid were added 9.5 g of 10% Pd/C and this mixture was hydrogenated at 50 psi and 65° C. for 16.5 h. Then the catalyst was filtered off and the filtrate was evaporated in vacuo. The oily residue was dissolved in water, rendered alkaline with conc. NaOH and extracted with $CHCl_3$. The organic layer was washed with brine, dried and evaporated to give 4.2 g of a crystalline solid, which was recrystallized with ethanol to yield 3.32 g (70%) 4,5-epoxy-14-hydroxy-N-methylmorphinan-6-one, m.p. 223°-225°, $[\alpha]_D^{26}$—267.6° (C 0.96, CHCl$_3$).

EXAMPLE 3

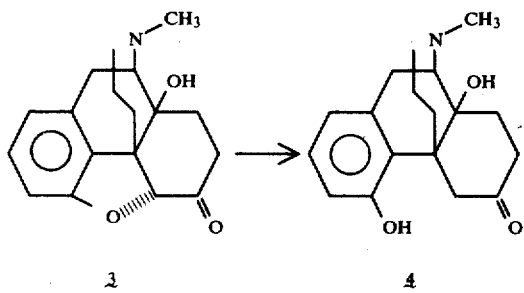

4,14-Dihydroxy-N-methylmorphinan-6-one

To a solution of 1.2 g (4.20 mmol) 4,5-epoxy-14-hydroxy-N-methylmorphinan-6-one in 36 ml ethanol 4.8 g (89.74 mmol) NH$_4$Cl were added and this mixture was stirred under reflux. During 15 min. 2.4 g (35.4 mg) activated zinc powder were added portionwise and the resulting mixture was refluxed for 0.5 h. After cooling to room temperature and filtration, the filtrate was evaporated. The residue was dissolved in water, basified with 10% NH$_4$OH and extracted with CHCl$_3$. The organic layer was washed with brine, dried and evaporated to give 1.1 g of a foam, which was crystallized with iso-propanol to yield 750 mg (62%) of 4,14-dihydroxy-N-methylmorphinan-6-one, m.p. 233°-236°, $[\alpha]_D^{26}$—149.3° (C 0.90, CHCl$_3$).

EXAMPLE 4

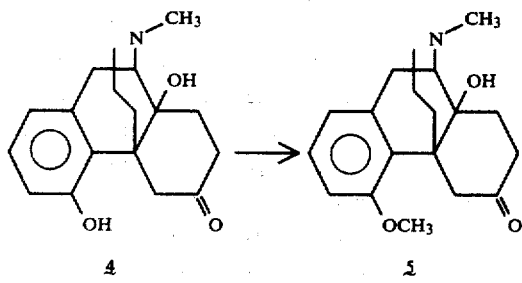

14-Hydroxy-4-methoxy-N-methylmorphinan-6-one

To a solution of 2.2 g (7.66 mmol) 4,14-dihydroxy-4-methoxy-N-methylmorphinan-6-one in 50 ml dry DMF were added 2.12 g (15.34 mmol) anhydrous K$_2$CO$_3$ and 3.96 g (23.07 mmol) phenyltrimethylammonium chloride and this mixture was stirred at 90° C. (bath temperature) for 4 h. After cooling to room temperature, the mixture was filtered, washed with CHCl$_3$ and evaporated (90° C. bath temperature). The residue was partitioned between ethyl acetate and water, the organic layer separated and washed with water, dried and evaporated to give 2.1 g of a crystalline residue. After recrystallization with ethanol 1.78 g (77%) of 14-hydroxy-4-methoxy-N-methylmorphinan-6-one, m.p. 191°-193°, $[\alpha]_D^{26}$—83.9° (C 0.88, CHCl$_3$) were obtained.

EXAMPLE 5

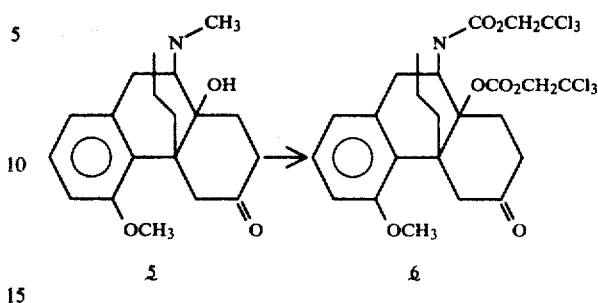

4-Methoxy-N,14-bis(2,2,2-trichloroethoxycarbonyl)-morphinan-6-one

To a solution of 1.75 g (5.81 mmol) 14-hydroxy-4-methoxy-N-methylmorphinan-6-one in 50 ml CHCl$_3$ 7 g (69.9 mmol) anhydrous KHCO$_3$ were added. While this mixture was refluxed and stirred, 8.75 ml (63.6 mmol) 2,2,2-trichloroethyl chloroformate was added dropwise during 10 min. under argon. This mixture was refluxed for 6 h., cooled and 50 ml of water was added. The organic layer was separated, washed with brine, dried and evaporated to give an oil, which was crystallized with ethyl acetate to yield 2.9 g (78%) 4-methoxy-N,14-bis(2,2,2-trichloroethoxycarbonyl)-morphinan-6-one, m.p. 115°-116°, $[\alpha]_D^{26}$—111.4° (C 0.93, CHCl$_3$).

EXAMPLE 6

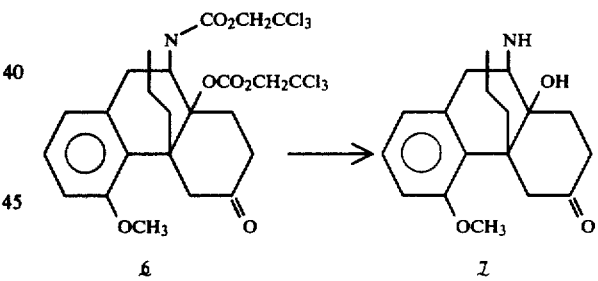

14-Hydroxy-4-methoxymorphinan-6-one

To a mixture of 2.9 g (4.54 mmol) 4-methoxy-N,14-bis(2,2,2-trichloroethoxycarbonyl)-morphinan-6-one in 130 ml ethanol were added 15 g (280.4 mmol) NH$_4$Cl and this mixture was stirred and refluxed. During 0.5 h 12 g (177 mg) activated zinc powder were added portionwise and the resulting mixture was refluxed for 1 h. After cooling and filtration, the filtrate was evaporated. The residue was dissolved in water, basified with saturated NaHCO$_3$ solution and extracted with CHCl$_3$. The organic layer was washed with brine, dried and evaporated to give an oil which was crystallized with isopropyl ether to yield 690 mg (53%) 14-hydroxy-4-methoxymorphinan-6-one, m.p. 137°-139°, $[\alpha]_D^{26}$—66.5°. (C 1.08, CHCl$_3$).

EXAMPLE 7

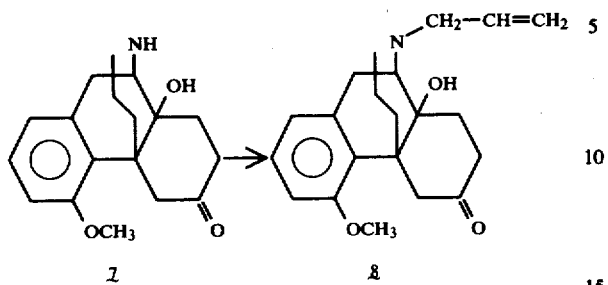

N-Allyl-14-hydroxy-4-methoxymorphinan-6-one

A mixture of 170 mg (0.59 mmol) 14-hydroxy-4-methoxymorphinan-6-one, 170 mg (1.23 mmol) anhydrous $K_2CO_3$ and 0.052 ml (0.60 mmol) allylbromide in 6 ml dry DMF was stirred at 90° C. (bath temperature) for 0.5 h. Then the mixture was filtered, washed with $CHCl_3$ and the filtrate was evaporated. The residue was partitioned between water and ether. The organic layer was separated and washed with brine, dried and evaporated to give 160 mg crystalline residue, which was washed with ethanol to yield 150 mg (78%) pure N-allyl-14-hydroxy-4methoxymorphinan-6-one, m.p. 166°–167°, $[\alpha]_D^{26}$—112.8° (C 0.90, $CHCl_3$).

EXAMPLE 8

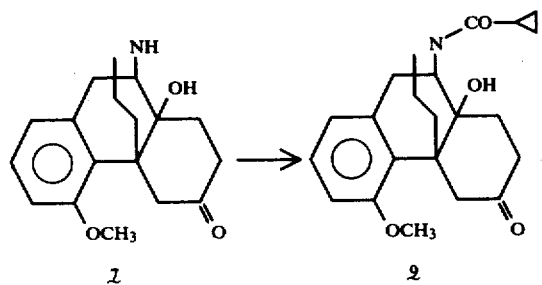

N-Cyclopropylcarbonyl-14-hydroxy-4-methoxymorphinan-6-one

To an ice-cooled mixture of 330 mg (1.15 mmol) 14-hydroxy-4-methoxymorphinan-6-one, 400 mg (2.89 mmol) anhydrous $K_2CO_3$ in 10 ml dry DMF was dropped a solution of 0.11 ml (1.21 mmol) cyclopropanecarboxylic acid chloride in 3 ml dry DMF during 10 min. while stirring. This mixture was stirred at 0° C. for an additional 50 min., then filtered, washed with $CHCl_3$ and the filtrate evaporated. The residue was partitioned between water and $CH_2Cl_2$, the organic layer separated, washed with brine, dried and evaporated. The resulting solid residue was crystallized with ethanol to give 350 mg (86%) N-cyclopropylcarbonyl-14-hydroxy-4-methoxymorphinan-6-one, m.p. 223°–225°, $[\alpha]_D^{26}$—167.2° (C 0.97, $CHCl_3$).

EXAMPLE 9

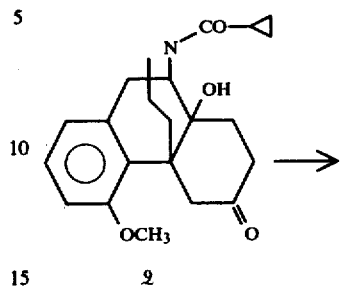

N-Cyclopropylmethyl-14-hydroxy-4-methoxymorphinan-6-one

To a suspension of 600 mg (15.8 mmol) LAH in 40 ml dry ether was added a solution of 250 mg (0.70 mmol) N-cyclopropylcarbonyl-14-hydroxy-4-methoxymorphinan-6-one in 5 ml dry $CH_2Cl_2$ dropwise during 15 min. at room temperature uner argon while stirring. This mixture was then refluxed for 4.5 h. Saturated $Na_2SO_4$ solution was added until all LAH was destroyed and the organic layer separated. The aqueous layer was extracted two times with either and the combined ether extracts were dried and evaporated to dryness to give 240 mg of a colorless oil of the epimeric carbinols 10, which was not further purified. A solution of this oil and 1.27 g (6.97 mmol) of benzophenol in 15 ml dry toluene was dropped to a slurry of 234 mg (2.09 mmol) KOtBu in 30 ml dry toluene at room temperature under argon while stirring. This mixture was stirred for 2.5 h. at 90° C. (bath temperature). After cooling, 20 ml 2 N HCl were added, the aqueous layer separated and the organic layer extracted 2 times with 5 ml 2 N HCl. The combined aqueous layers were washed with ether, basified with conc. NaOH and extracted with ether. The organic layer was washed with brine, dried and evaporated to give 210 mg of a semi-crystalline solid, which was treated with isopropyl ether to yield 170 mg (71%) pure N-cyclopropylmethyl-14-hydroxy-4-methoxymorphinan-6-one, m.p. 133°–135°, $[\alpha]_D^{26}$—108.6° (C 0.80, $CHCl_3$).

EXAMPLE 10

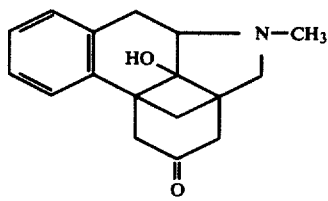

Conversion of 4,14-dihydroxy-6-keto-N-methylmorphinan into the phenyltetrazolyl ether followed procedures given in Example 1, and the removal of the phenyltetrazolyl ether group followed procedures given in Example 2, affording 14-hydroxy-6-keto-N-methylmorphinan, m.p. 143°–144°, $[\alpha]_D^{26}$ —137.9 (c 0.94, CHCl$_3$).

We claim:

1.

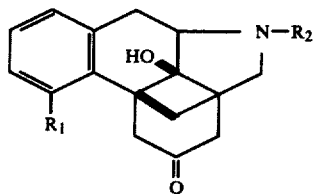

where
- $R_1$ = H, O lower alkyl, or O lower acyl
- $R_2$ = Lower alkyl, lower alkenyl, cyclopropylmethyl, or Ph lower alkyl.

2.

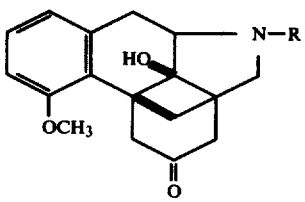

where
- R = methyl, phenethyl, allyl, cycloalkylmethyl wherein alkyl is C$_3$–C$_6$, dimethylallyl, alkynyl, or H.

3. The compound according to claim 2 wherein R is methyl.

4. The compound according to claim 2 wherein R is allyl.

5. The compound according to claim 2 wherein R is cyclopropylmethyl.

6. The compound according to claim 2 wherein R is cyclobutylmethyl.

7. The compound according to claim 2 wherein R is hydrogen.

8.

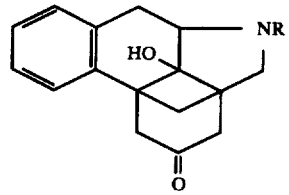

where
- R = methyl, phenethyl, allyl, cycloalkylmethyl, dimethylallyl, alkynyl, or H.

* * * * *